US005844005A

United States Patent [19]

Bauman et al.

[11] Patent Number: 5,844,005

[45] Date of Patent: Dec. 1, 1998

[54] HYDROCARBON SYNTHESIS USING REACTOR TAIL GAS FOR CATALYST REJUVENATION

[75] Inventors: Richard F. Bauman, Baton Rouge, La.; Charles W. DeGeorge, Chester; Rocco A. Fiato, Basking Ridge, both of N.J.; Stephen C. Leviness, Baton Rouge, La.

[73] Assignee: Exxon Research and Engineering Company, Florham Park, N.J.

[21] Appl. No.: 850,564

[22] Filed: May 2, 1997

[51] Int. Cl.[6] .................. C07C 27/00; B01J 20/34

[52] U.S. Cl. .................. 518/700; 502/21; 502/22; 502/30

[58] Field of Search .................. 518/700; 502/21, 502/22, 30

[56] References Cited

U.S. PATENT DOCUMENTS

| | | | |
|---|---|---|---|
| 5,260,239 | 11/1993 | Hsia | 502/30 |
| 5,268,344 | 12/1993 | Pedrick et al. | 502/30 |
| 5,283,216 | 2/1994 | Mitchell | 502/30 |
| 5,348,982 | 9/1994 | Herbolzheimer et al. | 518/700 |
| 5,545,674 | 8/1996 | Behrmann et al. | 518/715 |

FOREIGN PATENT DOCUMENTS

| | | |
|---|---|---|
| 2299767 | 10/1996 | United Kingdom . |

*Primary Examiner*—Brian M. Burn
*Assistant Examiner*—J. Parsa
*Attorney, Agent, or Firm*—Jay Simon

[57] ABSTRACT

Hydrogen containing tail gas from a hydrocarbon synthesis reactor is used as a hydrogen containing catalyst rejuvenating gas. If CO is present, the CO content, is less than 10 mole % of the gas and the $H_2$ to CO mole ratio is greater than 3:1. At least a portion of the water and liquid hydrocarbons are removed from the tail gas, before it is used to rejuvenate the reversibly deactivated catalyst.

37 Claims, 1 Drawing Sheet

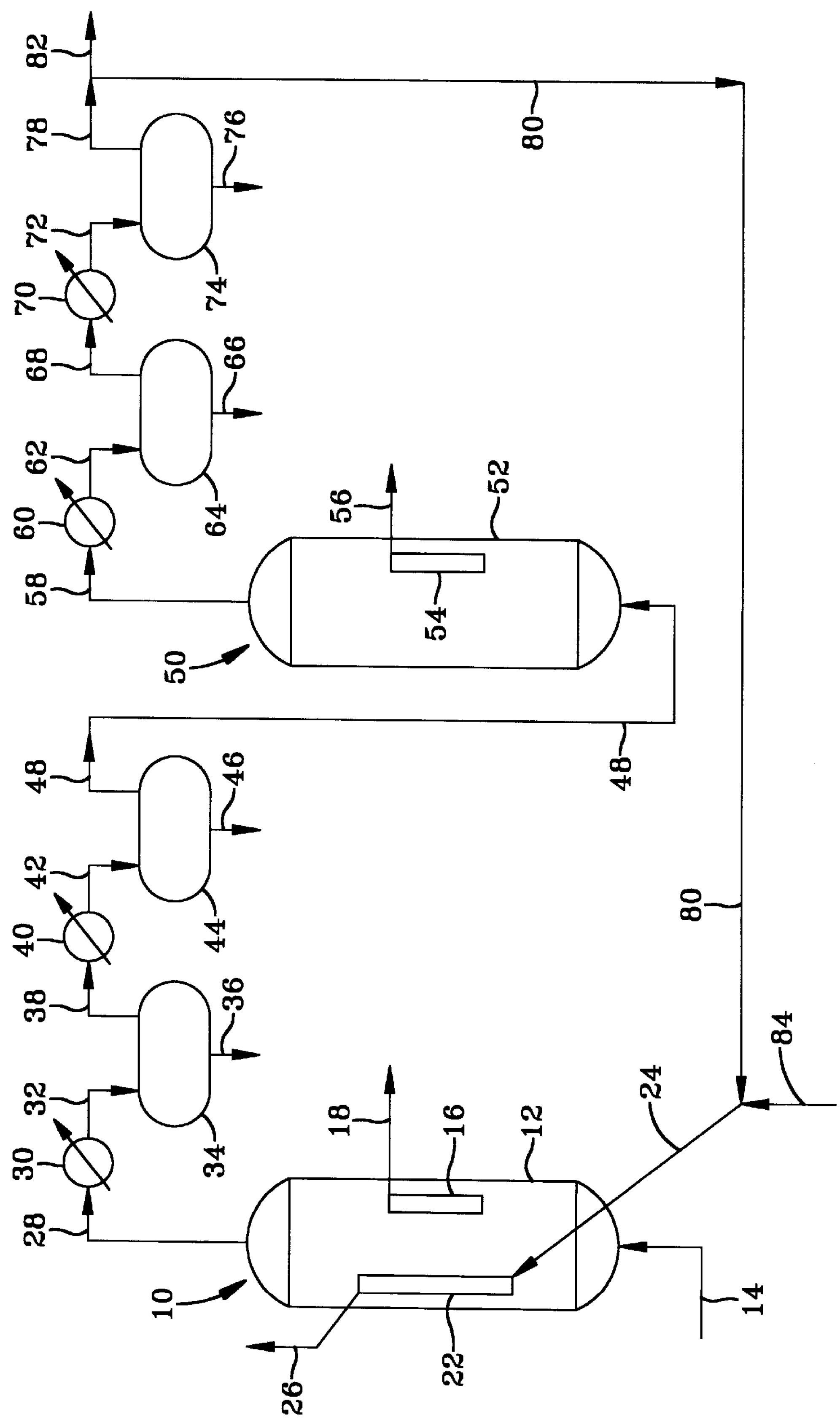
10
12
14
16
18
22
24
26
28
30
32
34
36
38
40
42
44
46
48
50
52
54
56
58
60
62
64
66
68
70
72
74
76
78
80
82
84

HYDROCARBON SYNTHESIS USING REACTOR TAIL GAS FOR CATALYST REJUVENATION

BACKGROUND OF THE DISCLOSURE

1. Field of the Invention

The invention relates to a hydrocarbon synthesis process using reactor tail gas for catalyst rejuvenation. More particularly, the invention relates to a slurry hydrocarbon synthesis process in which the solid, particulate catalyst is rejuvenated in the slurry liquid using a hydrogen containing rejuvenating gas comprising hydrocarbon synthesis reactor tail gas, from which a portion of the water and liquid hydrocarbons have been removed.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. Syngas made from hydrocarbon feedstocks which contain nitrogen (i.e., natural gas) or nitrogen containing compounds (i.e., resids, coal, shale, coke, tar sands, etc.) invariably contains HCN and/or $NH_3$ which rapidly, but reversibly, deactivate the catalyst. Certain oxygenates and carbonaceous compounds which are formed in the slurry as by-products of the HCS reaction are also believed to cause rapid deactivation. Catalyst deactivation by these species is reversible and catalytic activity is restored (the catalyst rejuvenated) by contacting the deactivated catalyst with hydrogen. The activity of the HCS catalyst in the reactive slurry may be intermittently or continuously rejuvenated by contacting the slurry with hydrogen or a hydrogen containing gas to form a rejuvenated catalyst slurry as is disclosed, for example, in U.S. Pat. Nos. 5,260,239; 5,268,344, and 5,283,216. Also, UK patent publication GB 2,299,767A discloses catalyst rejuvenation in a continuous stirred tank reactor, which is a fully backmixed reactor, by slightly increasing the amount of hydrogen in the synthesis gas from an $H_2$ to CO ratio of 2:1 or 2:1, up to 2.15:1 and by decreasing the syngas flow into the reactor, so that all of the CO is consumed. However, this process requires a regeneration time of from 12 to 24 hours and the fully backmixed conditions do not duplicate the conditions in a commercial size reactor.

SUMMARY OF THE INVENTION

The invention relates to rejuvenating a reversibly deactivated hydrocarbon synthesis (HCS) catalyst using a hydrogen containing catalyst rejuvenating gas comprising HCS reactor tail gas. More particularly, the invention comprises a process for rejuvenating a reversibly deactivated HCS catalyst by contacting the catalyst with a rejuvenating gas comprising $H_2$ and one or more diluents and in which, if CO is present, the $H_2$ to CO mole ratio is greater than 3:1 and the CO concentration is less than 10 mole %, wherein the rejuvenating gas comprises HCS reactor tail gas from which at least a portion and preferably most of the water vapor and liquid hydrocarbons have been removed. By liquid hydrocarbons is meant hydrocarbons which are liquid at standard conditions (e.g., 25° C. and 1 atm.) of temperature and pressure Since HCS reactors are typically operated at less than 100% CO conversion, the reactor tail gas contains unreacted $H_2$ and CO. The amount of $H_2$ present in the rejuvenating gas must be greater than that required to consume CO in the gas and, in the case of a slurry HCS process, any CO present in the slurry during the rejuvenation, to insure that sufficient $H_2$ remains to at least partially rejuvenate the catalyst. This is because the catalyst will not be rejuvenated until the CO is consumed. Sufficient $H_2$ must be present in the rejuvenating gas to achieve these objectives and still have unreacted $H_2$ remaining in the gas to prevent catalyst deactivation, which can occur if the catalyst are not maintained in contact with $H_2$. HCS reactor tail gas will typically be consumed as fuel, in a flare, or sent back to synthesis gas (syngas) generation. Therefore, it provides an efficient and inexpensive source of $H_2$ for catalyst rejuvenation. The tail gas can be from, and used to rejuvenate catalyst in, a fixed bed, fluid bed or slurry HCS reactor. In a slurry HCS process, the tail gas is from one or more slurry HCS reactors and the particulate HCS catalyst is rejuvenated in the slurry liquid either in the reactor, or in an external rejuvenation zone, such as an external vessel or lift pipe. The slurry comprises catalyst particles and gas bubbles in a hydrocarbon slurry liquid. Inerts, such as $CH_4$, $N_2$, and $CO_2$ present in processed tail gas do not interfere with the rejuvenation reaction. However, excessive amounts of inerts in the rejuvenation gas reduce the $H_2$ partial pressure in the gas and thereby the efficiency of the rejuvenation.

Tail gas from an HCS reactor, such as a slurry HCS reactor, typically contains water vapor, $CO_2$, $CH_4$, $N_2$, unreacted syngas ($H_2$ and CO), hydrocarbon products which are liquid at standard conditions of temperature and pressure, and $C_1$–$C_5$ hydrocarbon products which are gas at these conditions, particularly methane. The water vapor can comprise as much as 50% of the tail gas. The rejuvenating gas used in the process of the invention comprises HCS reactor tail gas from which at least a portion and preferably most of the water vapor, liquid hydrocarbon products and, optionally, a portion or all of the $CO_2$, are removed, before it is used to rejuvenate the catalyst in the slurry. With a stoichiometric ratio of $H_2$ to CO in the syngas feed, the $H_2$ to CO ratio in the tail gas exiting the reactor is also stoichiometric. In order to be useful for catalyst rejuvenation, the $H_2$ to CO mole ratio must be greater than 3:1, preferably greater than 4:1 and more preferably greater than 5:1. Tail gas having an $H_2$ to CO mole ratio of greater than 3:1 may be obtained by a variety of known methods. Hydrogen can be added. A syngas having an $H_2$ to CO mole ratio greater than stoichiometric can be used, in combination with operating the HCS reaction in multiple stages. Other methods for reducing the CO content and/or increasing the $H_2$ content of the tail gas include physical and chemical means such as, (i) adsorbing the CO with adsorbent beds or absorption by chemical scrubbing, (ii) cryogenic separation, (iii) steam reforming or passing at least a portion of the tail or other gas through a water gas shift reactor in which the CO reacts with water vapor to produce $H_2$ and $CO_2$. If the partial pressure of the $H_2$ is too low for efficient rejuvenation, all or part of the $CO_2$ may be removed from the gas by known means, such as amine scrubbing. Tail gas from which all or almost all the CO has been removed is particularly preferred, but this is not always feasible.

In a broad sense the invention comprises a process for rejuvenating a reversibly deactivated HCS catalyst by contacting the catalyst with a rejuvenating gas comprising HCS reactor tail gas comprising $H_2$ and one or more diluents and in which, if CO is present, the $H_2$ to CO mole ratio is greater than 3:1 and the CO concentration is less than 10 mole %. With respect to a hydrocarbon synthesis process not limited to a slurry process, the invention comprises reacting a synthesis gas comprising a mixture of $H_2$ and CO in the presence of a hydrocarbon synthesis catalyst and one or more catalyst deactivating species, at reaction conditions effective to form hydrocarbons from the gas and wherein the deactivating species at least partially reversibly deactivate the catalyst during the synthesis reaction, followed by contacting the reversibly deactivated catalyst with a catalyst rejuvenating gas comprising hydrocarbon synthesis reactor tail gas to at least partially rejuvenate the catalyst, wherein the rejuvenating gas comprises hydrogen and at least one diluent, and in which the mole ratio of $H_2$ to CO in said gas is greater than 3:1 and the CO concentration is less than 10 mole %. In a more specific embodiment with particular reference to a slurry HCS process, the invention comprises the steps of:

(a) reacting a synthesis gas comprising a mixture of $H_2$ and CO in the presence of one or more catalyst deactivating species and a hydrocarbon synthesis catalyst in a slurry at reaction conditions effective to form hydrocarbons from said gas, at least a portion of which are liquid at said reaction conditions, wherein said slurry comprises said catalyst and gas bubbles in a hydrocarbon slurry liquid comprising said liquid hydrocarbons, and wherein said species reversibly deactivate said catalyst and form a deactivated catalyst slurry during said reaction, and (b) contacting said deactivated catalyst slurry with a rejuvenating gas comprising a hydrocarbon synthesis reactor tail gas, to at least partially rejuvenate said catalyst and form a rejuvenated catalyst slurry, said rejuvenating gas comprising hydrogen and at least one diluent and in which the mole ratio of $H_2$ to CO in said gas is greater than 3 and the concentration of CO is less than 10 mole %.

It is preferred in the practice of the invention that the catalyst rejuvenation occur under non-shifting conditions in which little or no water gas shift reaction occurs. While the conditions for suppressing a water gas shift reaction will depend somewhat on the HCS catalyst being rejuvenated, in general these conditions include a temperature less than about 250° C. and the presence of at least 5 mole %, and preferably at least 10 mole % $CO_2$ in the rejuvenating gas, if CO is also present in the gas. By a CO concentration of less than 10 mole % is meant to include no CO in the gas, as well as CO present in the gas in an amount of less than 10 mole %. The water gas shift reaction to form $CO_2$ will not occur in the absence of CO. Thus, in yet another embodiment, the invention relates to a process for reducing and preferably preventing a water gas shift reaction during the catalyst rejuvenation process, by conducting the rejuvenation in the presence of $CO_2$ in an amount sufficient to suppress the water gas shift reaction.

BRIEF DESCRIPTION OF THE DRAWING

The FIGURE is a schematic block diagram of a two stage slurry hydrocarbon synthesis process using the process of the invention in which tail gas is used for slurry catalyst rejuvenation.

DETAILED DESCRIPTION

In a Fischer-Tropsch HCS process, a syngas comprising a mixture of $H_2$ and CO is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_{5+}$–$C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–40,000 V/hr/V, expressed as standard volumes of the gaseous CO and $H_2$ mixture (0° C., 1 atm) per hour per volume of catalyst, respectively. Slurry catalyst rejuvenation conditions of temperature and pressure are similar to those for hydrocarbon synthesis and are disclosed in the prior art. The syngas may be formed by various means known to those skilled in the art and need not be further explained. Irrespective of the source, syngas typically contains catalyst deactivating species such as $NH_3$ and HCN. As the prior art teaches, deactivation by these species is reversible and the catalyst can be rejuvenated by contacting it with hydrogen. This restoration of the catalytic activity of a reversibly deactivated catalyst is referred to as catalyst rejuvenation. However, while preferred and possible, complete restoration of the catalytic activity for all of the catalyst particles in the slurry passing through a rejuvenation tube may not always be achieved in the process of the invention. It's for this reason the expression "at least partially rejuvenates the catalyst particles therein" and the like, are used herein.

The prior art teaches that the hydrogen or hydrogen containing rejuvenating gas will preferably not contain CO, because CO present must be consumed by reacting it with hydrogen in the presence of the catalyst, before it can be rejuvenated. This wastes both the $H_2$ and CO by forming primarily methane, due to the high $H_2$ to CO ratio which results from the CO consumption. However, since tail gas contains valuable $H_2$ and is typically recycled to syngas generation or burned as fuel or in a flare, its availability makes it convenient to use for catalyst rejuvenation, provided the $H_2$ to CO mole ratio is greater than 3:1, preferably greater than 4:1 and more preferably greater than 5:1 as set forth above. Another advantage of using tail gas for catalyst rejuvenation particularly in an HCS slurry, is that the presence of inerts or diluents such as the $CO_2$, $N_2$, $CH_4$ and the like, serve as a lift gas for the rejuvenation to insure slurry circulation through the rejuvenation zone (such as a tube, lift pipe, or other means), without having to rely only on costly hydrogen.

The process of the invention may be conducted under shifting or non-shifting conditions in the rejuvenation zone, although non-shifting conditions are preferred. Shifting will occur if CO is present in the rejuvenating gas and if the amount of $CO_2$ present is less than 5–10 mole %. By shifting is meant a water gas shift reaction in which CO reacts with water vapor to produce $H_2$ and $CO_2$. While the conditions for suppressing a water gas shift reaction will depend somewhat on the particular HCS catalyst being rejuvenated, in general these conditions include (i) a temperature of no more than about 250° C., (ii) the substantial absence of CO, or (iii) $CO_2$ present in an amount sufficient to prevent the shift reaction (i.e., >5 mole % and preferably >10 mole %) in the rejuvenating tail gas. Typical commercial syngas feeds contain at least 2–3 mole %, and more usually 5–10 mole % $CO_2$, unless $CO_2$ removal prior to hydrocarbon syntheses is practiced, although this is usually not economical. The presence of this much $CO_2$ will generally prevent water gas shift from occurring over Co catalysts, except at very high temperatures (e.g., >500° F.). This is based on studies conducted with a commercial size slurry HCS reactor which cannot be predicted or duplicated by the use of laboratory equipment. A commercial slurry HCS reactor will typically be 20 or more feet high and 5 or more feet in diameter, with temperatures and reactant concentrations varying from top to bottom. It is not a backmixed system to the extent of a CSTR.

UK patent publication GB 2,299,767A discloses a periodic batch rejuvenation process in a CSTR laboratory reactor, in which the amount of hydrogen in the synthesis gas is slightly increased from an $H_2$ to CO ratio of 2:1 or 2:1, up to 2.15:1 and the syngas flow into the reactor is decreased, so that all of the CO is consumed. In contrast and by way of an illustrative, but nonlimiting example, for a slurry HCS reactor containing a supported Co metal catalyst in a hydrocarbon slurry liquid, the stoichiometric $H_2$ to CO mole ratio is 2.1:1. Even at a mole ratio of, e.g., 2.2, 2.5 or 2.9:1, all of the CO is not consumed by the HCS reaction in a commercial size reactor, unless the feed flow rate of synthesis gas is very low; the temperature is very high, and/or substantial water gas shift reaction occurs to consume CO while producing $H_2$. Therefore, gas having these low $H_2$ to CO mole ratios cannot be used for catalyst rejuvenation in a commercial size reactor. Further, the fully backmixed conditions in a CSTR laboratory reactor in which the temperature and reactant concentrations are constant throughout cannot be applied to a commercial size slurry HCS reactor, in which the syngas concentration decreases and the gas products of the HCS reaction increase as the gas bubbles rise up through the slurry. While it is possible, as a practical matter, 100% CO conversion typically is not achieved in a commercial size reactor, unless the $H_2$ to CO ratio is very high (e.g., at least >3:1). A high ratio favors the undesired formation of methane and hydrogenolysis of the valuable liquid hydrocarbons formed by the synthesis reaction. Commercial size reactors are typically designed for a synthesis gas flow rate in a range based on a desired hydrocarbon production. If this flow rate is decreased enough for all the CO to be consumed, catalyst attrition and weeping down through the gas distributor will occur. Therefore, the teaching of this patent publication is not applicable to either the process of the present invention or a commercial size HCS reactor.

The FIGURE is a schematic block diagram of a two stage slurry hydrocarbon synthesis process according to one embodiment of the invention which employs syngas having an $H_2$ to CO mole ratio greater than stoichiometric, in which $H_2$ and CO containing tail gas from the second stage HCS reactor is cooled to condense and separate water and $C_{5+}$ hydrocarbons from the gas, which is then recycled back to the first stage reactor as a rejuvenation gas. The first stage slurry reactor 10 comprises a cylindrical vessel 12 which contains an HCS slurry (not shown) within. A syngas feed line 14 passes a syngas comprising a mixture of $H_2$ and CO into the bottom of the reactor from where it is injected up into the bottom of the slurry as bubbles by suitable gas injection means (not shown) and reacts in the presence of the solid catalyst particles in the slurry liquid to form hydrocarbons, at least a portion of which are liquid at the reaction conditions. The liquid hydrocarbons are separated from the slurry by suitable means, such as one or more filters either in the slurry in the reactor or in an outboard filtration vessel, as is known to those skilled in the art. In this particular embodiment, one or more liquid filters briefly illustrated as box 16 are immersed in the reactive slurry and the liquid hydrocarbon products are withdrawn from the reactor via line 18 and upgraded by fractionation and/or one or more conversion operations into more valuable products, or sold neat. The syngas fed into the first stage reactor comprises a mixture of $H_2$ and CO in which the $H_2$ to CO mole ratio is greater than the stoichiometric ratio required to have just enough hydrogen to react with and consume all of the CO, if the reactor was operating at 100% conversion. In the practice of the invention, the first stage reactor is operated at less than 100% conversion (by conversion is meant the mole % CO which reacts with the $H_2$ in the syngas feed in the reactor to produce hydrocarbons) to provide unreacted $H_2$ and CO in the tail gas removed overhead via line 28. Further, in order to obtain a tail gas in which the $H_2$ to CO mole ratio is greater than stoichiometric without either adding $H_2$ to the gas or removing CO, the mole ratio of the $H_2$ to the CO in the syngas feed must be greater than stoichiometric, as will be explained in greater detail below. Unreacted $H_2$, CO and gas products of the HCS reaction pass up through the slurry into the top portion of the reactor and are withdrawn via gas product line 28 as tail gas. Due to the greater than stoichiometric mole ratio of the $H_2$ to the CO in the syngas feed, the mole ratio of the $H_2$ to CO in the tail gas exiting the first stage is greater than that in the syngas feed entering the reactor. In a two stage hydrocarbon synthesis plant in which the tail gas from the first stage reactor(s) comprises the feed gas to the second stage reactor (s), the amount of syngas fed into the first stage reactor(s) and the CO conversion in the first stage must be such as to insure a sufficient amount of unreacted syngas in the first stage tail gas to supply the syngas feed requirements to the second stage, with little and preferably no syngas make-up from the syngas plant. In the practice of the invention, adding make-up syngas from the plant feeding the first stage to the second stage will lower the $H_2$ to CO ratio in the second stage tail gas used for catalyst rejuvenation. This will reduce the $H_2$ to CO mole ratio in the second stage tail gas. A slurry catalyst rejuvenation means 22, such as one or more vertical rejuvenation tubes, is schematically shown inside reactor 10. The rejuvenation tube has means (not shown) for injecting a combination catalyst rejuvenation and lift gas comprising the water and hydrocarbon-reduced second stage tail gas into the tube via line 24. The catalyst particles in the slurry flowing up through the rejuvenation tube 22 are at least partially rejuvenated and the hydrogen containing rejuvenation offgas, which contains catalyst deactivating species, is removed from the rejuvenation means and reactor via line 26 and burned as fuel, in a flare or recycled as feed to the syngas generation facility. In another embodiment (not shown), the rejuvenation offgas is not burned, but is combined with the tail gas removed from the reactor and sent to the two stage cooling and separation. This recovers the hydrogen and slightly increases the $H_2$ to CO ratio in the tail gas ultimately fed into the reactor as rejuvenation gas. All or most of the catalyst deactivating species are removed with the aqueous condensate from the two stage, hot and cold condensation and separation shown. If necessary, a water scrubber may be employed to remove remaining catalyst deactivating species before the gas is fed into the next HCS stage or used for rejuvenation. The tail gas removed from the first stage reactor is passed, via line 28, through a heat exchanger 30 in which it is cooled to condense some of the water vapor and $C_{5+}$ hydrocarbons out of the gas as liquids. The mixture of condensed liquids and the remaining gas is passed via line 32 into separator 34 in which the liquids are removed from the bottom via line 36 and the gas removed overhead via line 38. The water and hydrocarbon reduced tail gas removed from separator 34 is passed through a second heat exchanger 40 via line 38 in which it is further cooled to condense and separate most of the remaining water and heavier $C_{5+}$ hydrocarbons from the gas, which are removed as condensate via line 46, with the water and $C_5$+ reduced tail gas fed into the bottom of second stage slurry HCS reactor 50 via gas feed line 48, in which it is bubbled up through the bottom of the HCS slurry (not shown) in the reactor, in a manner much the same as for the first stage reactor. In reactor 50, the first stage tail gas comprising a mixture of $H_2$ and CO in which the $H_2$ to CO mole ratio is at least stoichiometric, contacts the catalyst particles in the slurry and at least a portion of the CO in the gas is converted into hydrocarbons, at least a portion of which are liquid at the reaction conditions. The second stage slurry reactor 50 also comprises a hollow outer shell 52 containing a three phase HCS slurry (not shown) and liquid filtration means 54 within for separating the liquid hydrocarbon products from the catalyst particles as filtrate, with the filtrate removed from the reactor via line 56 and upgraded by fractionation and/or or more conversion operations to more valuable products, etc. Second stage reactor 50 is also operated at less than 100% CO conversion, so that tail gas exiting the reactor contains unreacted $H_2$ and CO, along with the gas products of the HCS reaction. The second stage reactor tail gas is removed overhead via gas line 58 and passed through a first heat exchanger 60 in which some of the water and $C_{5+}$ hydrocarbon products are condensed to liquids. The $H_2$ to CO ratio in the second stage tail gas is greater than in the first stage tail gas for two reasons. First, the ratio in the first stage tail gas is greater than the superstoichiometric ratio in the syngas fed into the first stage, due to the CO conversion in the first stage and the superstoichiometric ratio of the syngas feed. This first stage tail gas is fed into the second stage. Due to the CO conversion in the second stage, the $H_2$ to CO mole ratio in the second stage tail gas is greater than that in the first stage. The gas and liquid mixture is passed from the first cooler 60 into first separator 64, via line 62. The liquid condensate is removed from the bottom of the separator via line 66. The water and hydrocarbon reduced tail gas comprising a mixture of $H_2$ and CO, in which the $H_2$ to CO ratio is greater than that in the first stage tail gas, is passed via line 68 through a second heat exchanger 70 to further cool the gas and condense out most of the remaining water and higher molecular weight hydrocarbons. The gas and liquid mixture is passed from second cooler 70 into second separator 74 via line 72, in which the liquids settle out of the gas and liquid mixture and are removed via line 76. The water and hydrocarbon reduced tail gas passes out of the separator 74 via line 78 and is passed to line 80 which feeds it into line 24 and from there into the one or more catalyst rejuvenation means 22 immersed in the first stage reactive slurry. The tail gas acts as both a lift gas to insure slurry circulation up through the rejuvenation means by virtue of the lifting action of the gas and as a catalyst rejuvenating gas.

Most of the water and hydrocarbon reduced second stage tail gas is bled off via line 82 and disposed of as fuel, in a flare or recycled as feed to the syngas generation facility. Less than half is recycled and used as rejuvenating gas. Since a second stage HCS reactor(s) is typically operated at a lower pressure than the first stage, a compressor (not shown) may be required to increase the pressure of the tail gas being fed into the first stage rejuvenation zone. In yet a further embodiment, $CO_2$ removal means, such as amine scrubbing which is well known to those skilled in the art and not shown for the sake of convenience, may be employed to remove a portion of the $CO_2$ in the tail gas passing through line 80 prior to the compressor. This will reduce the compressor duty and also increase the $H_2$ partial pressure in the gas to provide more efficient catalyst rejuvenation, by reducing the dilution effect of the $CO_2$. In a further embodiment (not shown), all or a portion of the CO in the second stage tail gas may be removed before it is passed into the rejuvenation zone. As mentioned above, this may be accomplished by known physical and/or chemical means. Catalyst rejuvenating means may also be employed in the one or more second stage HCS reactors. This is optional and may not be required in some cases, inasmuch as the two-stage cooling, condensing and liquid separation from the rest of the tail gas between the HCS reactor stages results in the catalyst deactivating species being removed from the gas. Such species include $NH_3$, perhaps HCN, oxygenates and the like, with the net result that most or all of these condensable and/or water removable catalyst deactivating species are removed from the gas in the gas-liquid separators. This means little or none of these species is present in the gas being fed into the second stage reactor(s) and rejuvenating means.

While this embodiment employs two stages of hydrocarbon synthesis, the invention is not intended to be limited to two stages, but may be practiced with one, two and more than two stages. The use of one, two and more than two stages is known and appreciated by those skilled in the art. Using more than one stage permits greater flexibility and more overall CO conversion than can be obtained with only in one stage. Two or more stages of hydrocarbon synthesis also reduces the heat transfer burden encountered using only a single stage, by spreading the heat removal of the exothermic hydrocarbon synthesis reaction over the two or more stages. This means that each stage can be run at conditions for optimum selectivity towards the desired products. It also reduces catalyst rejuvenation requirements primarily to the first stage. Further, while only a single reactor is shown in the FIGURE for the two stage embodiment, more than one reactor may be, and more typically will be, used for each stage. As an illustrative, but nonlimiting example, the first stage may employ three or more reactors and the second stage two or more reactors. This permits a reactor to be taken off line for maintenance and repairs without having to shut down the entire HCS process. Finally, although the above illustration is for a slurry HCS process; the invention is not intended to be so limited, but may also be practiced with fixed and fluid bed processes.

As disclosed in U.S. Pat. No. 5,288,673, the degree of catalyst rejuvenation can be controlled by independently controlling the slurry temperature in the rejuvenating zone irrespective of the temperature of the main body of slurry in the surrounding HCS reaction zone. This patent discloses that temperature control in the rejuvenation zone or tubes is achieved by one or more of either increasing or decreasing the slurry residence time in the zone, so as to utilize the exothermic nature of the rejuvenation reactions, by insulating the rejuvenation tubes, by introducing heat or a cooling medium into the zone, by preheating the rejuvenating gas, etc. The '673 patent teaches that the temperature in the rejuvenation zone should be high enough to remove CO and at least partially rejuvenate the catalyst and low enough to minimize methane formation and wax (~$C_{20+}$ alkanes) hydrogenolysis. These teachings apply to the present invention also.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

The invention will be further understood with respect to the examples below, each of which is based on the two stage HCS reactor system described and shown in the FIGURE.

EXAMPLES

Comparative Example

In this example, which is a comparative example illustrating the practice of the prior art and which employs an HCS catalyst comprising Co as the catalytic metal which is composited with titania and supported on an alumina support, the syngas entering the first stage slurry reactor 10 comprises a mixture of $H_2$ and CO in the stoichiometric mole ratio of 2.1:1 for this process. The slurry reactor operates at 80% CO conversion. On a basis of 100 moles of syngas per unit of time fed into the reactor, the gas composition is 59 moles of $H_2$, 28.1 moles of CO and 12.9 moles of inerts. The inerts comprise about 0.6 moles of water vapor, 5.4 moles of $CO_2$, 3.4 moles of $N_2$ and 3.5 moles of $CH_4$. At an 80% conversion level, the tail gas exiting the reactor has a composition of 11.8 moles of $H_2$, 5.6 moles of CO and 37.2 moles of inerts, of which about 62% is water vapor resulting from the HCS reaction. The tail gas is passed through a first stage hot condenser 30 which cools the stream to about 280° F. and condenses out most of the water and $C_{5+}$ hydrocarbons, with the water and hydrocarbon reduced tail gas then passed through the first stage cold condenser operating at a temperature of about 120° F. to remove more water and other condensibles, leaving only 14 moles of inerts in the gas. This tail gas is passed into the second stage reactor 50 which also operates at 80% conversion. The exiting tail gas is sequentially passed, via lines 58, et. seq., through the hot and cold coolers and separators operating at the same temperatures as for the first stage tail gas. As a result, the hydrocarbon and water reduced tail gas available to be passed through lines 80 and 24 into the first stage catalyst rejuvenation means 22, comprises 2.4 moles of $H_2$, 1.1 mole of CO and 14 moles of inerts comprising primarily $CO_2$, $CH_4$ and $N_2$, with minor (less than 3% combined total) amounts of higher molecular weight hydrocarbons. The mole ratio of the $H_2$ to CO in the recycle tail gas is only the stoichiometric 2.1:1. In this case, the recycle tail gas does not contain enough $H_2$ to consume the CO in the rejuvenation zone, with enough left over to at least partially rejuvenate the catalyst in the slurry circulating up through it. Thus, the tail gas is not useful for rejuvenating the catalyst unless substantial amounts of hydrogen are added to it or if CO is removed.

EXAMPLE 1

This example demonstrates the effectiveness of the invention. In this example, the reactor sizes, conversion levels, catalyst, etc., in short, everything but the mole ratio of the $H_2$ to the CO in the syngas feed is identical to that of the Comparative Example above, including the temperatures of the hot and cold heat exchangers and separators. In this example, the ratio of the $H_2$ to the CO in the syngas fed into the first stage slurry reactor 10 is 2.2:1. On a basis of 100 moles of syngas feed per unit of time fed into the reactor, the amount of $H_2$ is 61.8 moles, the CO is 28.1 moles and the inerts are 12.9 and have the same composition as in the example above. The tail gas exiting the reactor 10 via line 28 contains 14.6 moles of $H_2$, along with 5.6 moles of CO and 37.2 moles of the inerts identical to the example above. After passing through the two heat exchangers 30 and 40 and respective separators 34 and 44, the gas is fed into the second stage reactor 50 which also operates at a conversion level of 80%, for a total combined conversion level of 96%. This is the same as for the example above. However, in this case, the tail gas passing out of separator 74 and into lines 78 and 80 contains 5.2 moles of $H_2$ and 1.1 moles of CO, along with 14 moles of inerts. Thus, the $H_2$ to CO mole ratio in the tail gas fed to the catalyst rejuvenation means in the first stage reactor is 4.7:1. The composition of the inerts is identical to that of the example above. The 4.7:1 mole ratio of the $H_2$ to CO in the tail gas is sufficient to consume the CO in the rejuvenation zone and at least partially rejuvenate the catalyst in the slurry passing up through the zone. Further, the presence of the inert gas (inert with respect to the rejuvenation reaction) provides sufficient gas flow up into the rejuvenation zone. Additional $H_2$ may be mixed with the second stage reactor tail gas and passed into the rejuvenation zone via lines 82 and 24, if desired. In this option, additional inert gas is not required to achieve lift in the rejuvenation zone.

In the practice of the invention as illustrated by the particular embodiment outlined above in which the catalyst in each stage comprises Co as the catalytic metal supported on titania and with specific reference to the FIGURE, if a syngas feed having a stoichiometric ratio of $H_2$ to CO of 2.1:1 is fed into the first stage reactor 10 and the 80% of the CO is converted to hydrocarbons, the $H_2$ to CO ratio in the tail gas stream removed from the first stage reactor via line 18 is still 2.1:1. This 2.1:1 mole ratio continues through the second stage, with the result that the second stage tail gas has the same mole ratio. Therefore it is necessary that the mole ratio of the syngas fed into the first stage be greater than stoichiometric. By using a syngas feed having an $H_2$ to CO ratio of 2.2:1, the $H_2$ to CO ratio in the first stage tail gas is a hydrogen rich 2.6:1 and the $H_2$ plus CO comprises 35% of the total tail gas composition. Passing the tail gas through the heat exchanger and separator doesn't change the 2.6:1 ratio in the tail gas, but increases the concentration of the $H_2$ and CO in the gas to 59%. This hydrogen rich tail gas, now reduced in water and hydrocarbons, is fed into the second stage reactor which also operates at 80% CO conversion, with the tail gas removed via line 58 having an $H_2$ to CO ratio of 4.7:1. After condensing out most of the water and hydrocarbons, a portion of this hydrogen rich tail gas is passed, via line 24 into the rejuvenation zone 14 in the first stage reactor in which it rejuvenates the catalyst activity.

EXAMPLE 2

This example is identical to that of Example 1 above, except that the $H_2$ to CO mole ratio in the syngas fed into the first stage reactor is 2.3:1, with the result that the tail gas exiting the reactor 10 via line 28 contains 17.4 moles of $H_2$, along with 5.6 moles of CO and 37.2 moles of the inerts identical to the Example above. The $H_2$ to CO mole ratio in the tail gas exiting the second stage reactor is 7.2:1, along with the inerts comprising $CO_2$, $CH_4$ and $N_2$ similar to Example 1. The total amount of the $H_2$ and CO in the tail gas available to be passed into and through lines 80, 24 and rejuvenation means 22, per arbitrary unit of time and based on 100 moles of the syngas passed into the first stage reactor 10 per same arbitrary unit of time, is about 9.2 moles (8.1 moles of $H_2$ and 1.1 moles of CO), along with about the same 14 moles of the inerts. In this example, the tail gas contains sufficient $H_2$ without the need for adding additional $H_2$ to it for catalyst rejuvenation.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for rejuvenating a reversibly deactivated hydrocarbon synthesis catalyst which comprises contacting said catalyst with a rejuvenating gas comprising hydrocarbon synthesis reactor tail gas containing $H_2$, CO and one or more diluents.

2. A process according to claim 1 wherein said tail gas contains water vapor and hydrocarbons, at least a portion of which are removed before it is used to rejuvenate said catalyst.

3. A process according to claim 2 wherein the CO concentration in said tail gas is less than 10 mole % and said $H_2$ to CO mole ratio is greater than 3:1.

4. A process according to claim 3 wherein said gas contains $CO_2$ in an amount greater than 5 mole % of the total gas composition.

5. A process according to claim 4 wherein said rejuvenation occurs under conditions in which little or no water gas shift reaction occurs.

6. A process according to claim 3 wherein said tail gas serves as both a rejuvenating gas and a lift gas for said regeneration.

7. A process according to claim 2 wherein a portion of said CO in said tail gas is removed or converted to $H_2$ and $CO_2$ prior to said rejuvenation.

8. A process according to claim 7 wherein said tail gas is steam reformed or passed through a water gas shift reactor in which the CO reacts with water to convert a portion of said CO to $H_2$ and $CO_2$ prior to said rejuvenation.

9. A process according to claim 2 wherein said tail gas also contains $CO_2$ and wherein a portion of said $CO_2$ is removed to increase the $H_2$ partial pressure prior to said rejuvenation.

10. A process according to claim 2 wherein said rejuvenation produces a hydrogen containing rejuvenation offgas which contains catalyst deactivating species and which is combined with said tail gas, and the combined gasses cooled to condense out water which contains most of said species and removing said water and species prior to said rejuvenation.

11. A process according to claim 2 wherein said hydrocarbons produced by said reaction include $C_{5+}$ liquid hydrocarbons, at least a portion of which are upgraded by fractionation or one or more conversion operations.

12. A process according to claim 5 wherein said rejuvenation occurs under non-shifting conditions.

13. A hydrocarbon synthesis process which comprises reacting a synthesis gas comprising a mixture of $H_2$ and CO, in the presence of a hydrocarbon synthesis catalyst and one or more catalyst deactivating species, in at least one stage and at reaction conditions effective to form hydrocarbons from said gas and wherein said deactivating species at least partially reversibly deactivate said catalyst during said synthesis reaction, followed by contacting said reversibly deactivated catalyst with a catalyst rejuvenating gas comprising tail gas comprising $H_2$ and CO in which the $H_2$ to CO mole ratio is greater than 3:1 to at least partially rejuvenate said catalyst, said tail gas having been obtained from a hydrocarbon synthesis reactor operated at less than 100% CO conversion using a synthesis gas feed in which the $H_2$ to CO mole ratio is greater than stoichiometric to produce said tail gas containing $H_2$ and CO, along with water vapor and gaseous hydrocarbons and in which the $H_2$ to CO mole ratio is greater than 3:1 and from which at least a portion of said water vapor and hydrocarbons have been removed.

14. A process according to claim 13 wherein said at least a portion of said water vapor and hydrocarbons are removed from said tail gas prior to said rejuvenation.

15. A process according to claim 14 wherein said hydrocarbons produced by said reaction include $C_{5+}$ liquid hydrocarbons, at least a portion of which are upgraded by fractionation or one or more conversion operations.

16. A process according to claim 15 wherein said CO concentration in said tail gas is less than 10 mole % and said tail gas also contains $CO_2$ in an amount greater than 5 mole %.

17. A process according to claim 16 wherein said rejuvenation occurs under conditions in which little or no water gas shift reaction occurs.

18. A process according to claim 14 wherein said tail gas serves as both a rejuvenation gas and a lift gas for said rejuvenation.

19. A process according to claim 14 wherein a portion of said CO in said tail gas is removed or converted to $H_2$ and $CO_2$ prior to said rejuvenation.

20. A process according to claim 19 wherein said tail gas is steam reformed or passed through a water gas shift reactor in which the CO reacts with water to convert a portion of said CO to $H_2$ and $CO_2$ prior to said rejuvenation.

21. A process according to claim 16 wherein a portion of said $CO_2$ in said tail gas is removed to increase the $H_2$ partial pressure prior to said rejuvenation.

22. A process according to claim 15 wherein said rejuvenation produces a hydrogen containing rejuvenation offgas which contains catalyst deactivating species and which is combined with said tail gas, and the combined gasses cooled to condense out water which contains most of said species and removing said water and species prior to said rejuvenation.

23. A process according to claim 17 wherein said rejuvenation occurs under non-shifting conditions.

24. A process according to claim 17 including two or more hydrocarbon synthesis stages all of which operate at less than 100% CO conversion, with said synthesis gas feed in which the $H_2$ to CO mole ratio is greater than stoichiometric is fed into said first stage and in which tail gas from each stage comprises the feed gas for the next successive stage, with the $H_2$ to CO mole ratio in each stage tail gas greater than that in the feed gas for that stage, and wherein tail gas from the last stage is used as the rejuvenating gas.

25. A slurry Fischer-Tropsch hydrocarbon synthesis process for producing hydrocarbons from a synthesis gas feed in at least two reaction stages which operate at less than 100% CO conversion, said feed gas for each stage comprising a mixture of $H_2$ and CO in which the $H_2$ to CO mole ratio is greater than stoichiometric and wherein said $H_2$ and CO are reacted in each stage in the presence of one or more catalyst deactivating species and a hydrocarbon synthesis catalyst in a slurry at reaction conditions effective to form hydrocarbons from said feed gas, at least a portion of which are liquid at said reaction conditions, wherein said slurry comprises said catalyst and gas bubbles in a hydrocarbon slurry liquid comprising said synthesized liquid hydrocarbons, wherein said species reversibly deactivate said catalyst and form a deactivated catalyst slurry during said reaction, wherein unreacted $H_2$ and CO along with gaseous reaction products are removed from each stage as tail gas in which the $H_2$:CO mole ratio is greater than that in the feed gas for that stage, wherein said tail gas comprises the synthesis gas feed for the next successive stage, and wherein the $H_2$ to CO mole ratio in the last stage tail gas is greater than 3:1, said process further comprising:

(a) passing said last stage tail gas back to the first stage, and (b) contacting said first stage deactivated catalyst slurry with said last stage tail gas to at least partially rejuvenate said catalyst in said slurry and form a catalyst rejuvenated slurry.

26. A process according to claim 25 wherein said tail gas contains water vapor and hydrocarbons, at least a portion of which are removed before is used to rejuvenate said catalyst.

27. A process according to claim 26 wherein said last stage tail gas contains $CO_2$ in an amount greater than 5 mole % of the total gas composition and wherein the CO concentration is less than 10 mole %.

28. A process according to claim 27 wherein said liquid hydrocarbons comprise $C_{5+}$ hydrocarbons, at least a portion of which are upgraded by fractionation or one or more conversion operations.

29. A process according to claim 28 wherein said rejuvenation is conducted under conditions in which little or no water gas shift reaction occurs.

30. A process according to claim 26 wherein said tail gas serves as both a rejuvenating gas and a lift gas for said rejuvenation.

31. A process according to claim 28 in which a portion of said CO in said tail gas is removed or converted to $H_2$ and CO prior to said rejuvenation.

32. A process according to claim 31 wherein said tail gas is steam reformed or passed through a water gas shift reactor in which the CO reacts with water to convert a portion of said CO to $H_2$ and $CO_2$ prior to said rejuvenation.

33. A process according to claim 29 wherein said tail gas also contains $CO_2$ and wherein a portion of said $CO_2$ is removed to increase the $H_2$ partial pressure prior to said rejuvenation.

34. A process according to claim 28 wherein said rejuvenation produces a hydrogen containing rejuvenation offgas which contains catalyst deactivating species and which is combined with said tail gas, and the combined gasses cooled to condense out water which contains most of said species and removing said water and species prior to said rejuvenation.

35. A process according to claim 28 wherein said rejuvenation occurs under non-shifting conditions.

36. The process of claim 16 wherein upgrading is effected by catalytic processing in the presence of hydrogen.

37. The process of claim 36 wherein the catalytic processing comprises hydroisomerization.

* * * * *